United States Patent [19]

Akama et al.

[11] Patent Number: 5,509,413
[45] Date of Patent: Apr. 23, 1996

[54] ULTRASONIC DIAGNOSTIC APPARATUS

[75] Inventors: Terufumi Akama; Yoichi Sumino, both of Tochigi, Japan

[73] Assignee: Kabushiki Kaisha Toshiba, Kawasaki, Japan

[21] Appl. No.: 286,329

[22] Filed: Aug. 5, 1994

[30] Foreign Application Priority Data

Aug. 11, 1993 [JP] Japan ................................. 5-199517
Sep. 2, 1993 [JP] Japan ................................. 5-218503

[51] Int. Cl.⁶ ....................................................... A61B 8/00
[52] U.S. Cl. ....................................................... 128/660.02
[58] Field of Search ........................ 128/660.02, 660.06, 128/660.07, 661.02, 660.08, 661.03, 662.02; 73/609, 610, 611, 631

[56] References Cited

U.S. PATENT DOCUMENTS 4,240,295  12/1980  Uranishi .............................. 128/660.08
4,359,056  11/1982  Carlson ............................... 128/661.03
4,700,571  10/1987  Okazaki .............................. 128/660.02

*Primary Examiner*—George Manuel
*Attorney, Agent, or Firm*—Finnegan, Henderson, Farabow, Garrett & Dunner

[57] ABSTRACT

For an ultrasonic wave to be transmitted, an ultrasonic probe driving unit can apply a stepwise varying drive voltage to the ultrasonic probe. The drive voltage of the driving unit is so selectively set by a setting unit as to allow the output level of the ultrasonic wave to be in a range below, but nearest to, an upper limit. It is, therefore, possible to obtain maximal image quality in a range in which safety is secured.

24 Claims, 3 Drawing Sheets

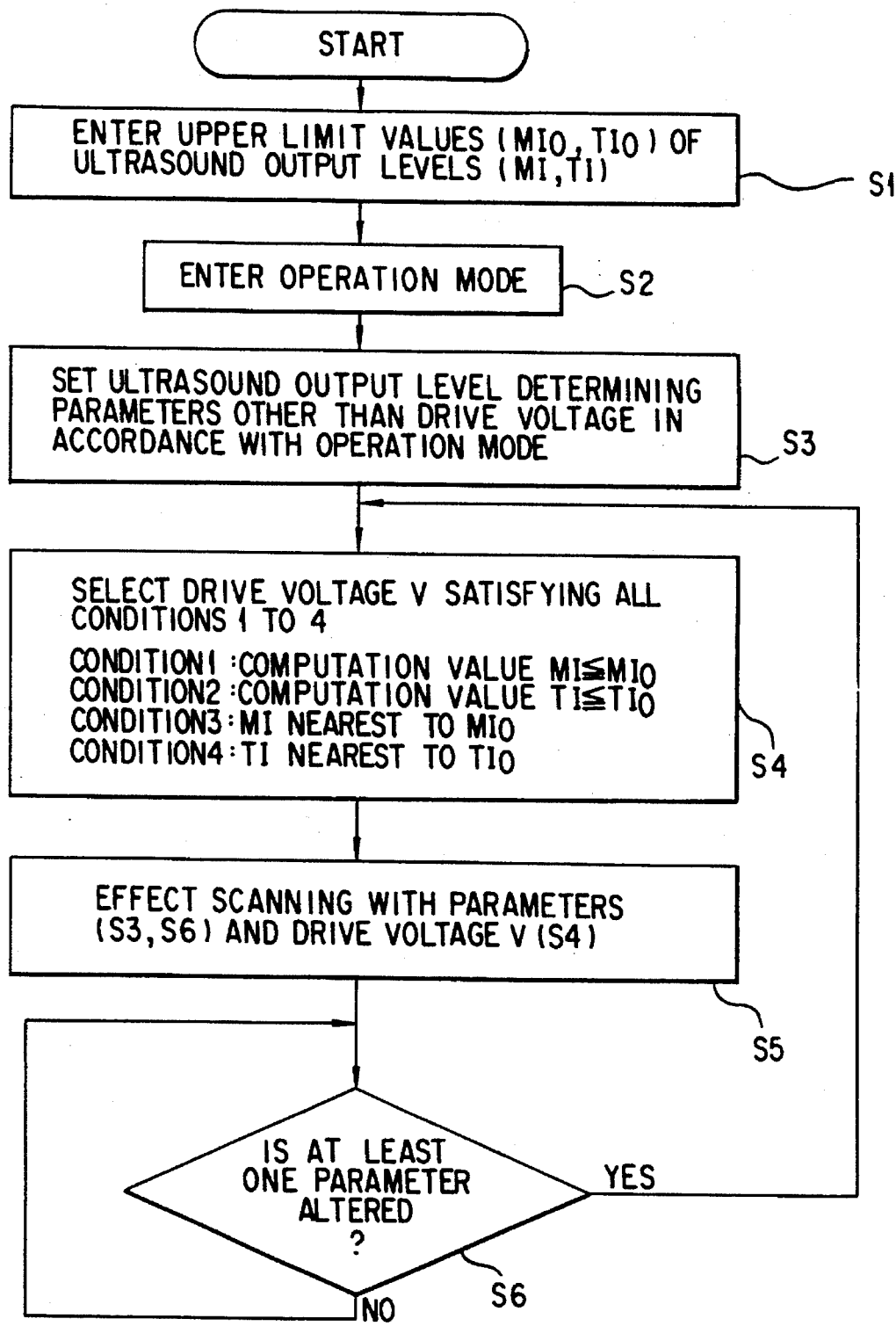
F I G. 4

ULTRASONIC DIAGNOSTIC APPARATUS

BACKGROUND OF THE INVENTION

1. Field of the Invention

The present invention relates to an ultrasonic diagnostic apparatus.

2. Description of the Related Art

An ultrasonic diagnostic apparatus generates an ultrasonic wave through its ultrasonic probe to allow it to propagate in a living body of a human subject, detects a corresponding echo at the probe and evaluates it for diagnostic purpose after being processed. Such a diagnostic examination by the ultrasound has been extensively utilized on the fetus of a pregnant woman. It is, therefore, necessary to fully check the safety of the apparatus in use.

With respect to the pulsed ultrasonic wave, the safety standard has been established based on the following various indexes:

Ispta (Spatial Peak Temporal Average Intensity)

Isppa (Spatial Peak Pulse Average Intensity)

Im (Maximum Intensity): the intensity of a wave of a maximum amplitude in one pulse MI (Mechanical Index): the index of mechanical damage by physical energy generated upon the bursting of bubbles formed under a negative pressure of a given ultrasonic wave (longitudinal wave).

TI (Thermal Index): the index of thermal damage caused by the evolution of heat upon the absorption of a given ultrasonic wave during propagation in the living body of the human subject.

These are indexes recommended by the FDA of the U.S.A. The indexes Ispta, Isppa and Im have been conventionally used among the users but, in recent years, these are being replaced with the new indexes MI and TI. Now is the time for the existing indexes to be changed to the new indexes, thus sometimes causing some confusion among the users.

The ultrasonic diagnostic apparatus having a measure of safety against a possible confusion is disclosed in JPN PAT. APPLN. KOKOKU PUBLICATION NO. 4-25013, JPN PAT. APPLN. KOKAI PUBLICATION NOs. 4-156832, 2-84944, 4-352953 and 3-146043, JPN UTILITY MODEL APPLN KOKAI PUBLICATION NO. 63-120611, etc. Of these publications, some are directed to the technique of adjusting the output level of an ultrasonic wave by the user and some to the technique of numerically displaying, together with an ultrasonic image, the output level of that ultrasonic wave. In these techniques, after the setting of the output level of a given ultrasonic wave it has not been possible to cope with the change of those parameters on the various output levels of the ultrasonic wave, such as replacing a probe with another kind of probe, changing a mode to another mode, varying the position of a transmission focus and changing the rate frequency. Since, in this case, those unaltered parameters, other than those already set out above, are maintained at their initial levels, the resultant output level of a given ultrasonic wave is higher than the initial-value. Therefore, various problems have been arisen due to a risk so that a given ultrasonic wave exceeds an output level that an operator has designed, a too low output level of a ultrasonic wave and hence a resultant poor image quality, etc.

SUMMARY OF THE INVENTION

One object of the present invention is to provide an ultrasonic diagnostic apparatus which can display indexes, associated with an ultrasonic output level, in a form understandable to a user.

Another object of the present invention is to provide an ultrasonic diagnostic apparatus which, even if at least one parameter associated with an ultrasound output level varies, can automatically adjust the ultrasound output level.

According to the present invention, there is provided an ultrasonic diagnostic apparatus for obtaining ultrasonic information by scanning an interior of a subject, by an ultrasonic probe, with an ultrasonic wave, comprising:

driving means for driving the ultrasonic probe to emit an ultrasonic wave to the subject, the driving means allowing a drive voltage which is applied to the ultrasonic probe to be varied stepwise;

input means for inputting the upper limit value of an output level of the ultrasonic wave; and setting means for selectively setting the drive voltage of the driving means such that the output level of the ultrasonic wave is equal or less than the upper limit value, and nearest to the upper limit value.

According to another embodiment of the present invention, there is also provided ultrasonic diagnostic apparatus for obtaining ultrasonic information by scanning an interior of a subject, by an ultrasonic probe, with an ultrasonic wave, comprising:

setting means for setting at least one parameter associated with the scanning;

calculating means for calculating an output level of an ultrasonic wave on the basis of the at least one parameter; and means for displaying, in real time, the ultrasonic information and the output level calculated by the calculating means.

In another embodiment of the present invention of claim 1, for an ultrasonic wave to be transmitted, an ultrasonic probe driving means can apply a stepwise varying drive voltage to the ultrasonic probe. The drive voltage of the driving means is so selectively set by setting means as to allow the output level of the ultrasonic wave to be in a range below, but nearest to, the upper limit value. It is, therefore, possible to obtain a maximal image quality in a range in which safety is secured.

In the invention of claim 10, the output level of the ultrasonic wave is calculated based on at least one parameter on the scanning operation set by the setting means. This contributes to securing safety because the output level, together with ultrasonic information, can be displayed in real time.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 4 is a flowchart of explaining the operation of controlling an ultrasound output level by a CPU in FIG. 1.

DETAILED DESCRIPTION OF THE PREFERRED EMBODIMENTS

An embodiment of the present invention will be explained below with reference to the accompanying drawings.

Figure 1:
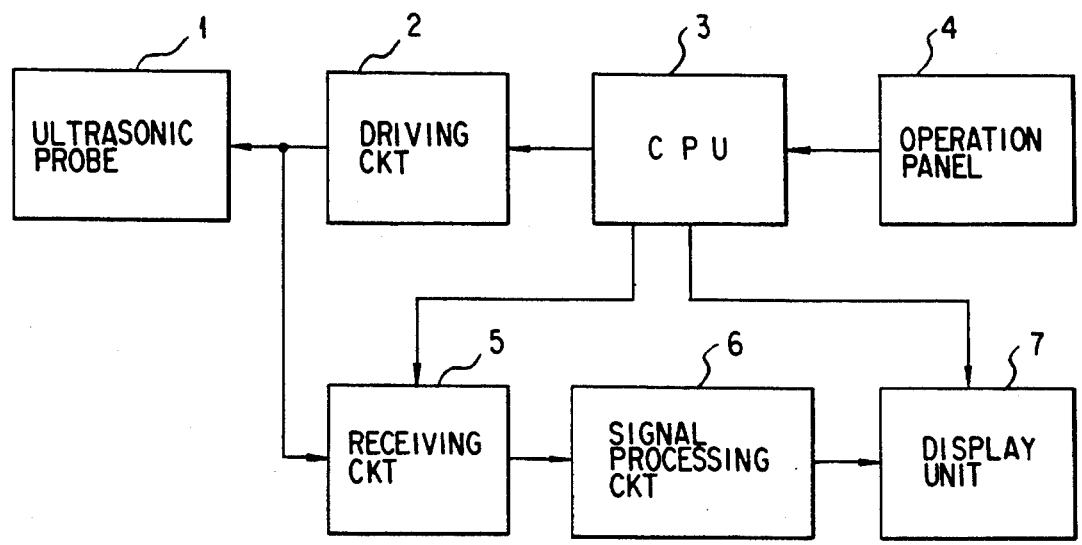
FIG. 1 is a block diagram showing an arrangement of an ultrasonic diagnostic apparatus according to an embodiment of the present invention.

FIG. 1 is a block diagram showing an arrangement of an ultrasonic diagnostic apparatus according to an embodiment of the present invention. An ultrasonic probe 1 is equipped at its forward end portion with an oscillation element array and adapted to transmit the beam of an ultrasonic wave to a subject to be examined, to receive a corresponding echo from the subject and to, after being converted to an electric signal, deliver the signal as an output. Here, the ultrasonic probe 1 will be explained below as corresponding to a sector scanning system, but this does not negate the application of it to a linear scan, etc.

Figure 2:
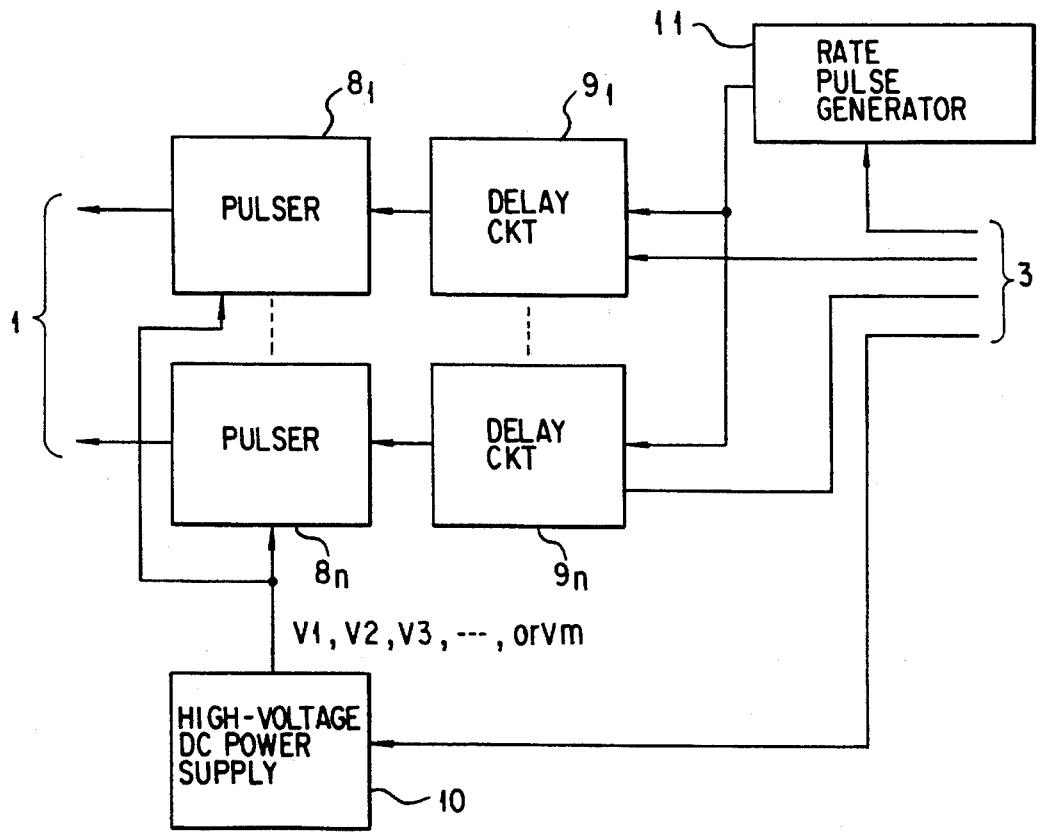
FIG. 2 is a block diagram showing an arrangement of a driving circuit of FIG. 1.

FIG. 2 shows an arrangement of a driving circuit for driving the ultrasonic probe 1 and allowing an ultrasonic beam to be emitted from the ultrasonic probe. A rate pulse generator 11 enables a clock pulse which is generated from a clock generator, not shown, to be subjected to a frequency division in accordance with a control signal from a CPU 3, for example, to generate a rate pulse with a rate frequency of 5 KHz. The rate pulse is sent to pulsers $8_1 \ldots 8_n$ via delay circuits $9_1$ to $9_n$ which are so provided as to correspond to oscillation elements in the oscillation element array of the ultrasonic probe 1. The delay circuits $9_2 \ldots 9_n$ impart delay times to the rate pulses in accordance with the azimuthal directions of the ultrasonic beam and their depth of focus. By charging capacitors with a power supply voltage from a high-voltage DC power supply 10 and discharging the capacitor in a timing in which the rate pulse is received, the pulsers $8_1 \ldots 8_n$ resonate corresponding resonant circuits including the oscillation elements to allow an ultrasonic wave to be emitted from each element of the ultrasonic probe 1. As the high-voltage DC power supply 10, use is made of a power supply whose output voltage (electromotive force) can be varied stepwise as v1, v2, ..., vn. In this case, any of these output voltages can be selected under control of a CPU 3.

Those echoes corresponding to ultrasonic pulses emitted into the living body of the subject are received by the corresponding elements of the oscillation element array of the same probe and converted to electric signals. The electric signals are given, by a reception delay circuit, corresponding delay times via amplifiers of respective elements in a reception circuit 5 and additively processed, noting that the delay times are given for ultrasound reception directivity and focusing. The output of the reception delay circuit is sent to a signal processing circuit 6.

The signal processing circuit 6 amplitude-detects the output of the reception delay circuit and generates a black/white B mode data at a B mode time, a two-dimensional bloodstream velocity data from the output of the reception delay circuit at a color flow mapping mode time and both the data at a both-modes combined B/C mode. The B mode data and two-dimensional cross-sectional data are displayed, as a light/shade tissue image and blood-stream velocity image respectively, on a high-definition monitor of a display unit 7. The method of how to generate a two-dimensional bloodstream is a technique well known as a color flow mapping and will be briefly explained below since this constitutes no major aspect of the present invention. The output of the reception delay circuit is multiplied by a reference signal of a fundamental frequency $f_0$ (for example, $f_0$=3.5 MHz) of an ultrasonic wave generated from a reference signal generator, through a mixer, and a resultant signal is passed through a lowpass filter to obtain a difference frequency (envelope), followed by the A/D conversion to a digital signal by means of an A/D converter. The reference signal is used as two kinds of signals 90° different in phase from each other. The signals are quadrature-detected through the mixer and lowpass filter to obtain signals corresponding to real and imaginary parts, followed by the A/D conversion and Doppler computation through an MTI filter. By so doing, it is possible to generate multi-point bloodstream velocity data (two-dimensional bloodstream velocity data). The MTI filter is used to eliminate an echo from a fixed (or slow-velocity) reflector, such as the cardiac muscle. Only a bloodstream signal passed through the MTI filter is subjected to Doppler computation. By so doing, bloodstream velocity data, such as an average bloodstream velocity, distributed velocity and power, are calculated at sample points (interval of, for example, 0.5 mm) for respective scanning lines.

CPU 3 has not only such a control/computation function as that of an ordinary CPU but also the following functions specific to the present invention. The first function is to select such a drive voltage as to allow the output level of the ultrasonic wave to be set as near to an upper limit level as possible in a range below the upper limit level and to secure safety and suppress decline in image quality. The second function is to do such a thing that, when at least one of a plurality of kinds of parameters for determining the output level of the ultrasonic wave is altered during scanning with the ultrasonic wave, a resultant variation in the output level of the ultrasonic wave is suppressed, by properly correcting at least one of the other parameters, so that it is possible to secure safety and suppress a degeneration in quality of an image obtained. The third function is to calculate a plurality of kinds of indexes representing the output levels of the ultrasonic wave and numerically display them on the display unit 7. The fourth function is to perform arithmetic operation on at least two indexes designated by the user, that is, perform operation on the indexes A and B, a relative ratio (A/B) finding, multiplication (A×B), addition (A+B) and difference (A−B) and numerically display them on the display unit 7.

Figure 3:
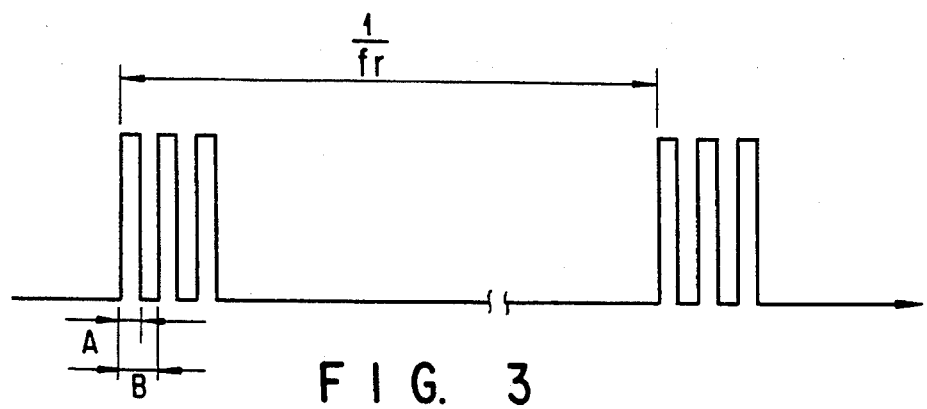
FIG. 3 is a view for explaining a rate frequency and burst wave.

A plurality of kinds of parameters for determining the output level of an ultrasonic wave include the position of a transmission focus for determining the depth of a field of vision (the depth of focus), repetition frequency of the beam of the ultrasonic wave in the same direction (the rate frequency fr: see FIG. 3), burst wave number of each rate, deflection angle of the beam of the ultrasonic wave, transmission aperture determined by the number of simultaneously driven oscillation elements, duty ratio of a burst wave (a ratio between a pulse width A and a pulse repetition cycle b: see FIG. 3), drive voltage of a power source, etc. The output level of the ultrasonic wave is calculated from these kinds of parameters.

The following are indexes representing the levels of the ultrasonic waves capable of being calculated:

Ispta (Spatial Peak Temporal Average Intensity)

Isppa (Spatial Peak Pulse Average Intensity)

Im (Maximum Intensity): the intensity of a wave of a maximum amplitude in one pulse MI (Mechanical Index): the index of mechanical damage by physical energy generated upon the bursting of bubbles formed under a negative pressure of an ultrasonic wave (longitudinal wave), the index above being obtainable from the following equation $$MI = Pr.3(z)/fc^{1/2}$$

where

Pr.3(z): the negative pressure (unit: WPa)

fc: the center frequency.

TI (Thermal Index): the index of thermal damage caused by the evolution of heat upon the absorption of a given ultrasonic wave during propagation in the living body of the subject, the index being obtainable from the following equation $$TI = WO/Wdeg$$

where

WO: the total temporal average intensity (unit: mW)

Wdeg: the power level (unit: mW) necessary to be raised by one degree.

An operation panel 4 operated by the user is connected to CPU 3. Through the operation panel 4 it is possible to select one of the B mode, color flow mapping mode and B/C mode, to designate at least one of the plurality of kinds of indexes to be displayed, to designate at least two indexes of the plurality of kinds of indexes to be used for ultrasound output level control, to set the upper limit of the output level of the ultrasonic wave, to designate at least one of arithmetic operations to be displayed, to designate two indexes to be used for arithmetic operations, to individually vary those parameters for determining the ultrasound output level other than a drive voltage and to select one of first and second display modes of different display elements. It is to be noted that all the elements in the first and second display modes may be displayed at a time on one image screen. In this case, it is not necessary to have the function of selecting one of the first and second display modes of the display elements.

The operation of the present embodiment will now be explained below.

FIG. 4 shows a flowchart for the automatic control for the ultrasound output level by CPU3. Before the start of effecting actual scanning, designation is given through the operation panel 4, for example, at least one index, say MI and TI, to be expressed of the plurality of kinds of indexes and at least two indexes, say MI and TI, to be used for ultrasound output level control, of the plurality of kinds of indexes. The upper limits of the ultrasound output level are also set as $MI_0$ to $TI_0$ —S1—and designation is given to at least one, say a division (relative ratio) and multiplication to be displayed (not shown), of the arithmetic operations and to two indexes, say Ispta and MI to be subjected to arithmetic operation, and one mode is selected out of the B mode, color flow mapping mode and B/C mode—S2.

In accordance with the selected operation mode, CPU 3 sets those parameters determining the ultrasound output level, other than the drive voltage, such as the depth of focus, rate frequency fr, burst wave number, deflection angle, transmission aperture and duty ratio—S3. The values of the parameters determining the ultrasound output level other than the drive voltage are installed in internal memory in CPU3 in accordance with the operation mode.

Based on the parameters, set at step S3, determining the ultrasound output level, as well as the upper limits $MI_0$ and $TI_0$ of the ultrasound output level, CPU 3 selects the greatest drive voltage vi ($1 \leq i \leq n$)—S4—in a range in which those calculated values MI and TI do not exceed $MI_0$ and $TI_0$. That is, the drive voltage Vi satisfying all the following conditions are selected.

Condition 1: $MI \leq MI_0$

Condition 2: $TI \leq TI_0$

Condition 3: MI nearest to $MI_0$

Condition 4: TI nearest to $TI_0$

The actual scanning is performed in accordance with the drive voltage Vi above and parameters (S3)—S5, thus generating an image corresponding to the operation mode for display. In this way, in the range in which the calculated values MI, TI do not exceed the upper limits $MI_0$ and $TI_0$, the scanning can be carried out with the greatest drive voltage Vi, thus enabling the highest image quality to be obtained in a range in which safety is secured.

There are sometimes the cases where, during scanning, at least one of the parameters determining the ultrasound output level other than the drive voltage is changed via the operation panel 4, such as the depth of visibility, is made great with an ROI (region of interest) of a subject displaced off the field of visibility and the operation mode is switched to another mode. CPU 3 determines, continuously or from time to time, whether or not at least one of the parameters determining the ultrasound output level other than the drive voltage is changed—S6. If, here, at least one of the parameters determining the ultrasound output level is changed and the determination at step S6 is in the affirmative, then control goes back to step S6 and the drive voltage satisfying all the conditions 1 to 4 is re-selected based on the parameters changed at step S6, parameters, other than the drive voltage, set at step S3 and not changed at step S6 and upper limits $MI_0$ and $TI_0$ of the ultrasound output level. Actual scanning is effected (S5) in accordance with the parameter changed at step S6, parameters, other than the drive voltage, set at step S3 and not changed at step S6, and re-selected drive voltages.

In this way, during scanning, even if at least one of the parameters determining the ultrasound output level is changed, the drive voltage is re-set and scanning is effected with the greatest drive voltage in a range in which MI and TI do not exceed the upper values $MI_0$ and $TI_0$. It is, therefore, possible to avoid the problem, such as the risk that an output level is higher than a level which an operator has design and the downgrading of an image quality due to the ultrasound output level of being made too low.

Figure 5A:
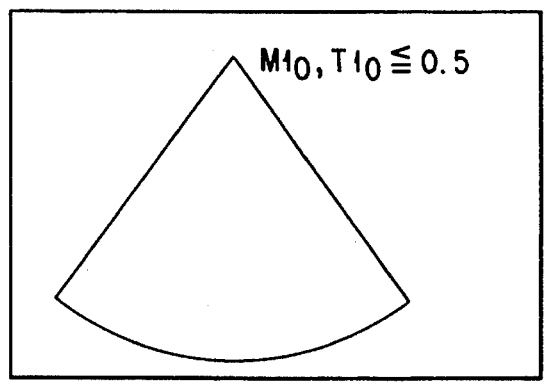
FIGS. 5A, 5B and 5C are views, each, showing a form of a display surface on a display unit of FIG. 1.
Figure 5B:
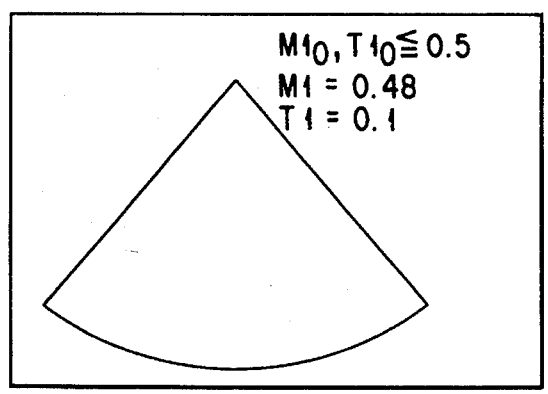

Next the displaying of the indexes will be explained below. Here, explanation will be made, as set out above, on the cases where designation is given to, say, MI and TI as at least one index to be displayed, of the plurality of kinds of indexes, the division (relative ratio) and multiplication to be expressed as at least one of the arithmetic operations and, say, Ispta and MI, as two indexes to be subjected to the arithmetic operation. FIG. 5A shows an input image surface of the upper limit value, FIG. 5B, an image surface of the first mode and FIG. 5C, an image surface of the second mode.

With the first mode selected, the upper limit values $MI_0$ and $TI_0$ and present MI and TI calculated from an actually selected drive voltage are numerically displayed together with an ultrasonic image. In order to set a drive voltage so as to make the actual index value correspond to the upper values $MI_0$ and $TI_0$, it is necessary to provide the high-voltage DC power supply 10 whose output voltage is adjustable in a stepless way, but this is technically difficult to achieve from the standpoint of a cost involved. In this way, the display of not only the upper limit values of $MI_0$ and $MI_0$ but also the actual values MI and TI can contribute to enhancing a safety level.

Figure 5C:
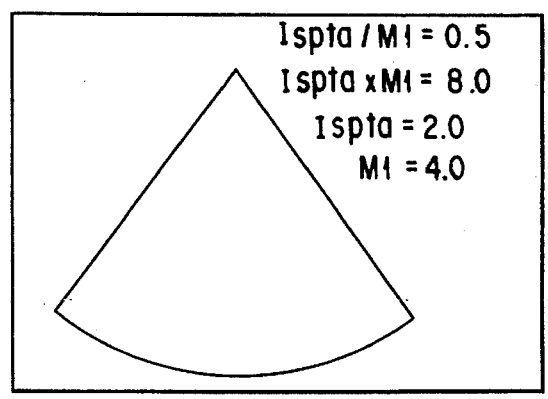

With the second mode selected, a result of division of Ispta by MI (relative ratio) and result of multiplication between these two and Ispta and MI are numerically displayed, together with the ultrasonic image, as shown in FIG. 5C. In this way, the user can represent a result of arithmetic operation on the designated two indexes. By designating one of existing indexes Ispta, Isppa and Im and one of the new indexes MI and TI as two indexes to be subjected to arithmetic operation, a resultant new index unfamiliar to the user can be recognized based on a familiar existing index. It is, therefore, possible for the user to confirm an adverse influence of an ultrasonic wave on the living body of a human subject and hence to contribute much to securing safety.

The present invention is not restricted to the previous embodiment and various changes and modifications of the present invention can be made without departing from the spirit and scope of the present invention.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An ultrasonic diagnostic apparatus for obtaining ultrasonic information by scanning an interior of a subject with an ultrasonic wave through an ultrasonic probe, an output level of the ultrasonic wave being determined on the basis of a first parameter and a second parameter, the first parameter being a drive voltage which is applied to the ultrasonic probe, comprising:

means for setting the second parameter, wherein the second parameter is selected from at least one of depth of focus, rate frequency, burst wave number transmission aperture and duty ratio of the ultrasonic wave; and means for controlling the drive voltage on the basis of the set second parameter such that the output level of the ultrasonic wave is equal to or less than a predetermined upper limit value.

2. The apparatus according to claim 1, wherein the output level of the ultrasonic wave is one of Ispta, Isppa, Im, MI and TI.

3. The apparatus according to claim 1, further comprising:

means for correcting the set second parameter during scanning wherein the setting means re-sets the drive voltage on the basis of the corrected set second parameter such that the output level is equal or less than the upper limit value.

4. The apparatus according to claim 1, wherein the output level of the ultrasonic wave contains at least two indexes, and the setting means sets the drive voltage to allow all of the indexes to be in a range below, but nearest to, the upper limit value.

5. The apparatus according to claim 1, in which the indexes are MI and TI.

6. The apparatus according to claim 1, further comprising:

drive means for applying the drive voltage to the ultrasonic probe, the drive means including a rate pulse generator for generating a rate pulse, a power supply variable stepwise in its output voltage, and a pulser for charging the output voltage of the power supply and for discharging it in a timing in which the rate pulse is received.

7. The apparatus according to claim 1, further comprising display means for displaying the output level corresponding to the set second parameter and the controlled drive voltage.

8. The apparatus according to claim 7, wherein the display means simultaneously displays the upper limit value and the output level.

9. The apparatus according to claim 1, wherein the output level of the ultrasonic wave contains two indexes $I1$, $I2$, and display means is further provided for displaying the two indexes corresponding to the controlled drive voltage.

10. The apparatus according to claim 9, further comprising:

means for calculating at least one of $I1+I2$, $I1-I2$, $I1/I2$ and $I1 \times I2$, and wherein said display means displays a result of the calculating means.

11. The apparatus according to claim 10, wherein one of the two indexes is one of Ispta, Isppa and Im and the other index is one of MI and TI.

12. The ultrasonic diagnostic apparatus according to claim 1 further comprising means for inputting the predetermined upper limit value.

13. The ultrasonic diagnostic apparatus according to claim 1, wherein said setting means includes means for designating one of a plurality of operation modes and means for determining the second parameter on the basis of the designated operation mode.

14. An ultrasonic diagnostic apparatus for obtaining ultrasonic information by scanning an interior of a subject with an ultrasonic probe using an ultrasonic wave, comprising:

means for setting at least one parameter associated with the scanning;

calculating means for calculating an output level of the ultrasonic wave on the basis of the at least one parameter, the output level of the ultrasonic wave being selected from one of Ispta, Isppa, MI and TI; and means for displaying, in real time, the ultrasonic information and the output level calculated by the calculating means.

15. The apparatus according to claim 14, wherein said at least one parameter is selected from at least one of the drive voltage of the ultrasonic wave and the depth of focus, rate frequency, burst wave number, transmission aperture and duty ratio of the ultrasonic wave.

16. The apparatus according to claim 14, wherein the output level of the ultrasonic wave contains two indexes $I1$ and $I2$;

the calculating means calculates the indexes on the basis of the at least one parameter; and the display means displays, in real time, the two indexes calculated by the calculating means.

17. The apparatus according to claim 16, wherein the calculating means calculates at least one of $I1+I2$, $I1-I2$, $I1/I2$ and $I1 \times I2$, and the display means displays, in real time, a result of the calculating means.

18. The apparatus according to claim 17, in which one of the two indexes is one of Ispta, Isppa and In and the other index is one of MI and TI.

19. An ultrasonic diagnostic apparatus for obtaining a tomographic image of an object comprising:

means for transmitting/receiving an ultrasonic wave to/from the object;

means for varying at least one of a plurality of parameters relating to an ultrasonic output level to maintain the output level below a predetermined upper output value when another one of the plurality of parameters is varied; and means for displaying the tomographic image wherein said ultrasonic output level is represented by at least one of a mechanical index MI representing a mechanical influence on the object by energy generated when a bubble bursts as it is expanded and contracted while an ultrasonic wave is propagated through the object, and a thermal index TI representing a thermal influence (an increase in temperature of the tissue) on the object by energy absorbed in the tissue of the object from the ultrasonic wave.

20. The ultrasonic diagnostic apparatus according to claim 19, wherein said plurality of parameters include a transmission focus position, a rate frequency, a transmission aperture, a burst-wave number, a duty ratio and a transmission voltage.

21. The ultrasonic diagnostic apparatus according to claim 19, wherein said ultrasonic output level is represented by at least one of a mechanical index MI representing a mechanical influence on the object by energy generated when a bubble bursts as it is expanded and contracted while an ultrasonic wave is propagated through the object, and a thermal index TI representing a thermal influence (an increase in temperature of the tissue) on the object by energy absorbed in the tissue of the object from the ultrasonic wave.

22. The ultrasonic diagnostic apparatus according to claim 19 or 21, wherein the varying means maintains the ultrasonic output level at a predetermined value.

23. The ultrasonic diagnostic apparatus according to claim 19 or 21, wherein ultrasonic output levels are calculated at all times based on said plurality of parameters, and are consecutively displayed on the display means.

24. The ultrasonic diagnostic apparatus according to claim 19 or 21, further comprising input means for setting said predetermined upper output level.

* * * * *

UNITED STATES PATENT AND TRADEMARK OFFICE
CERTIFICATE OF CORRECTION

PATENT NO. : 5,509,413
DATED : April 23, 1996
INVENTOR(S) : Terufumi AKAMA et al It is certified that error appears in the above-indentified patent and that said Letters Patent is hereby corrected as shown below:

In Claim 1, column 7, line 44, after "number",
insert --,--.

Signed and Sealed this

Twenty-sixth Day of November 1996

BRUCE LEHMAN

Attest:

Attesting Officer         Commissioner of Patents and Trademarks